United States Patent
Aoki

[19]

[11] Patent Number: 5,989,919
[45] Date of Patent: Nov. 23, 1999

[54] METHOD FOR ANALYZING CONTAMINATION WITHIN HOLE IN SEMICONDUCTOR DEVICE

[75] Inventor: Hidemitsu Aoki, Tokyo, Japan

[73] Assignee: NEC Corporation, Tokyo, Japan

[21] Appl. No.: 08/828,965

[22] Filed: Mar. 27, 1997

[51] Int. Cl.⁶ .................................................. G01N 33/20
[52] U.S. Cl. .................... 436/73; 436/79; 436/83; 436/84; 436/171; 134/1.3; 438/14; 438/756
[58] Field of Search .................................. 436/73, 79, 83, 436/84, 171, 172, 173; 134/1.3; 438/14, 756; 216/84

[56] References Cited

U.S. PATENT DOCUMENTS

| | | | |
|---|---|---|---|
| 4,990,459 | 2/1991 | Maeda et al. | 436/178 |
| 5,527,707 | 6/1996 | Fukazawa | 436/72 |
| 5,686,314 | 11/1997 | Miyazaki | 436/177 |
| 5,877,027 | 3/1999 | Kemmochi et al. | 436/175 |
| 5,890,501 | 4/1999 | Kaneko et al. | 134/1.3 |

FOREIGN PATENT DOCUMENTS 61-82436  4/1986  Japan .

OTHER PUBLICATIONS

"A new Technique for Quantitative Analysis of Metallic Contamination inside Deep–Submicron–Diameter Holes", H. Aoki, pp. 154–156, Extended Abstracts of the 1996 International Conference on Solid State Devices and Materials, Yokohama, Dec. 1996.

*Cleaning Technology of Surface of Silicon Wafer,* p. 97, (Japanese language with English language translation) Nov. 1995.

*Primary Examiner*—Randy Gulakowski
*Assistant Examiner*—Anita Alanko
*Attorney, Agent, or Firm*—J. Warren Whitesel; Laff, Whitesel & Saret, Ltd.

[57] ABSTRACT

First and second semiconductor substrate samples formed with a first oxide layer with holes and a third semiconductor substrate sample formed with a second oxide layer having no hole are prepared. The first and the third samples are subject to the same contaminating process for contaminating the surface of the first oxide layer of the first sample and the surface within the hole, and the surface of the second oxide layer of the third sample. All of the first and second layers of the first to third samples are dissolved by the HF vapor. The dissolved solutions are collected and analyzed the amount of contaminating material contained in respective solutions. The contamination amount in the hole is derived from the first, second and third contamination amount from an equation:

contamination amount in the hole =first contamination amount–second contamination amount–(surface exposing ratio×third contamination amount)

By this, in the process of fabrication of the semiconductor product, metal contaminant within the hole can be analyzed with high sensitivity, and can monitor washing effect.

9 Claims, 6 Drawing Sheets

METHOD FOR ANALYZING CONTAMINATION WITHIN HOLE IN SEMICONDUCTOR DEVICE

BACKGROUND OF THE INVENTION

1. Field of the Invention

The present invention relates to a method for analyzing contamination within a hole in semiconductor device suitable for analyzing metal contamination within a fine hole formed on a semiconductor substrate.

2. Description of the Related Art

Associating with integration of semiconductor device, contact hole and through hole are down-sized and an aspect ratio is progressively increasing. In 1 Gbit dynamic semiconductor random access memory device (1 Gbit DRAM), it has been considered to be required hole having aspect ratio of 5 to 10 at an opening diameter of 0.15 $\mu$m of the contact hole and the through hole. It is important technology for improving reliability of the device, to wash out metallic contaminant presenting within the fine hole and having high aspect ratio.

In order to develop a new washing liquid which can wash out metallic contaminant in fine hole, it is required to judge whether the metallic contaminant within the hole could be satisfactorily removed utilizing a typically used acid washing liquid, such as sulfonic hydrogen peroxide solution or the like and what extent a new washing liquid to be used in combination with surface active agent is effective. Therefore, technology for analyzing metal contamination amount within the hole is important for developing new washing liquid.

Currently, as a technology for making analysis of metallic contaminant amount, an atomic absorption method, an inductively coupled plasma (ICP) mass analyzing method and a X-ray fluorescence total reflection analyzing method are employed. All of these methods are technology for analyzing metallic contaminant amount presenting on the surface of the semiconductor layer. Among these methods, atomic absorption method permits measurement of metallic contaminant amount presenting on the surface of the semiconductor substrate by dissolving natural oxide layer on the surface of the semiconductor substrate by HF vapor or the like, collecting the solution, and analyzing metallic contaminant amount in the solution by atomic absorption measurement device. Similarly, ICP mass analyzing method makes analysis of the metallic contaminant amount in the collected solution by ICP mass.

Such atomic absorption method and ICP mass method can analyze metallic contaminant amount depositing on the semiconductor substrate having no irregularity. However, it is not possible to analyze contaminant amount residing within the hole.

On the other hand, XPS method and atomic spectrum analysis (AES) method irradiating a beam of X ray or the like in the fine region of the surface of the semiconductor substrate are low in detection sensitivity with respect to contaminant and cannot detect contamination unless the surface contaminant concentration is greater than or equal to $10^{14}$ atoms/cm$^2$.

In the current semiconductor cleaning technology, contaminant concentration less than or equal to $10^{10}$ atoms/cm$^2$ is required. Accordingly, it has been required a method for measuring contamination in the fine hole at high sensitivity and preparation method of a sample for analysis.

SUMMARY OF THE INVENTION

It is therefore an object of the present invention to provide a method for analyzing metal contaminant within a hole in the semiconductor substrate with high sensitivity.

A contamination analyzing method within a hole in the semiconductor device, according to the present invention, comprises the steps of:

preparing first and second semiconductor substrate samples having a first layer with holes on said first and second semiconductor substrate samples and a third semiconductor substrate sample having a second layer with no hole on said third semiconductor substrate;

subjecting the first semiconductor substrate sample and the third semiconductor substrate sample to the same contaminating process for contaminating the surface of the first layer of the first semiconductor substrate sample and the surface within the hole, and the surface of the second layer of the third semiconductor substrate sample;

dissolving all of the first and second layers of the first to third semiconductor substrate samples, collecting solutions after dissolving, analyzing amount of contaminating material contained in respective solutions for obtaining first to third contamination amount with respect to the first to third semiconductor substrate samples; and deriving a contamination amount within the hole of the first semiconductor substrate sample from the first to third contamination amounts.

In the step of obtaining contamination amount, the contamination amount in the hole is derived on the basis of the first, second and third contamination amount from an equation:

$$\text{contamination amount in hole} = \text{first contamination amount} - \text{second contamination amount} - (\text{surface exposing ratio} \times \text{third contamination amount}) \quad (1)$$

wherein the surface exposing ratio is a surface ratio [1−(occupying ratio of the hole)] of exposed surface in the first semiconductor substrate sample.

When the contamination amount of the second semiconductor substrate sample is much smaller in comparison with the contamination amount of the first and third semiconductor substrate samples, the contamination amount within the hole may be derived from an equation:

$$\text{contamination amount in hole} = \text{first contamination amount} - (\text{surface exposing ratio} \times \text{third contamination amount}) \quad (2)$$

It is preferred that before dissolving the layer formed on the first, second and third semiconductor substrate sample, layers depositing on the side surface and back surface of each semiconductor substrate sample are removed.

Also, dissolving of the layer may be performed with a vapor containing HF.

The contaminating material may be a metal.

The contaminant amount contained in the dissolved solution may be measured by one of atomic absorption measurement device and an ICP analyzing device, The first to third semiconductor substrate samples may be formed of Si and the first and second layers are oxide layers of Si.

The contaminating process may be dipping of the first to third semiconductor substrate samples within contaminating solution.

By employing the contamination analyzing method according to the present invention, the metal contamination amount within the hole formed in the first layer of the first semiconductor substrate sample as object for analysis can be analyzed. Accordingly, in the present invention, it becomes possible to know the effect of washing of inside of the hole of the conventional washing liquid and newly developed washing liquid.

Also, since the analyzing method according to the present invention is not depend on the hole diameter or hole depth, even for the quite fine hole and quite deep hole, information concerning the contamination or effect of washing can be obtained at a quite high sensitivity, namely contamination amount of lower than or equal to $10^{10}$ (atoms/cm$^2$).

BRIEF DESCRIPTION OF THE DRAWINGS

The present invention will be understood more fully from the detailed description given herebelow and from the accompanying drawings of the preferred embodiment of the invention, which, however, should not be taken to be limitative to the present invention, but are for explanation and understanding only.

In the drawings.

DESCRIPTION OF THE PREFERRED EMBODIMENT

The present invention will be discussed hereinafter in detail in terms of the preferred embodiment of the present invention with reference to the accompanying drawings. In the following description, numerous specific details are set forth in order to provide a thorough understanding of the present invention. It will be obvious, however to those skilled in the art that the present invention may be practiced without these specific details. In other instance, well-known structures are not shown in detail in order to avoid unnecessary obscure the present invention.

Figure 1A:
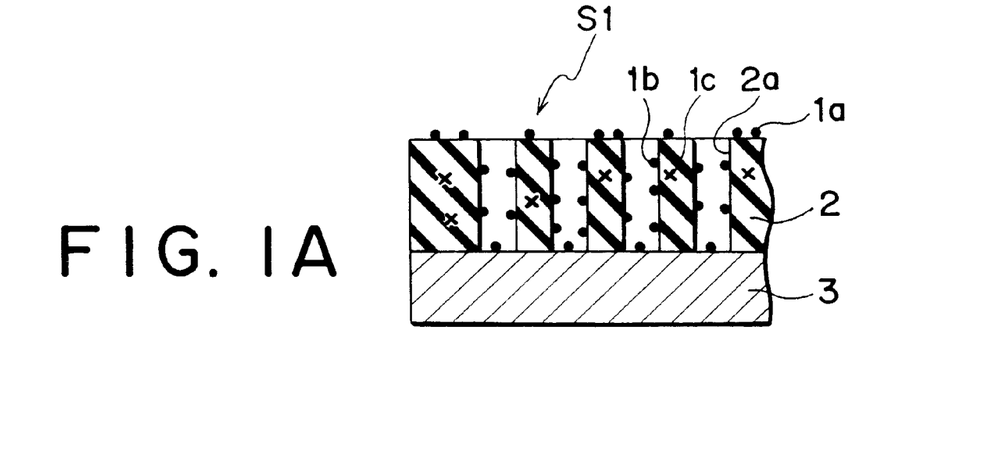
FIGS. 1A to 1C are sections showing a semiconductor substrate sample to be used in the preferred embodiment of a contamination analyzing method within a hole according to the present invention.
Figure 1B:
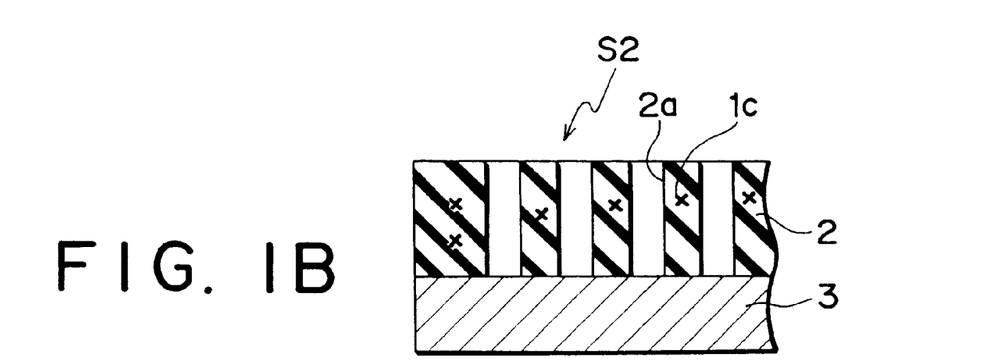
Figure 1C:
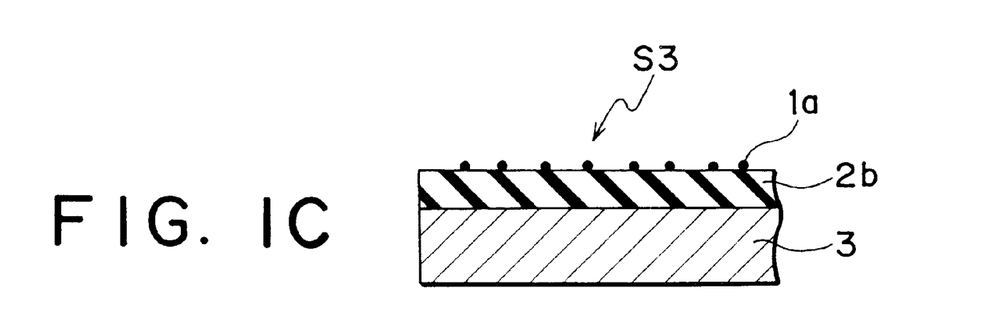

FIGS. 1A to 1C are sections showing a semiconductor substrate sample to be used in the preferred embodiment of a contamination analyzing method within a hole according to the present invention. FIG. 1A shows a first semiconductor substrate sample S1 as an object for analysis, for which analysis of contamination within a hole is to be performed. FIG. 1B shows a second semiconductor substrate sample S2 which has the same shape but is not subject contaminating process. FIG. 1C is a section showing the third semiconductor substrate sample S3 having a second layer which has no hole.

As shown in FIG. 1A, in the first semiconductor sample S1, an insulative oxide layer 2 (first layer) is formed on the surface of a semiconductor substrate 3. In the oxide layer 2, holes 2a are formed. As subjected to the contaminating process, contaminant consisted of metals 1a and 1b is caused on the surface of the oxide layer 2 and within the hole 2a.

It should be noted that, separately from the contaminating process, during process of step for forming the oxide layer 2, the contamination metal 1c is also caused within the oxide layer 2.

As shown in FIG. 1B, the second semiconductor substrate sample S2 has a layer structure and structure same as that in the first sample S1. However, since the second sample S2 is not subject the contaminating process, no metallic contamination will be caused in the semiconductor substrate sample S2. However, there should present the contaminating metal 1c penetrating during the fabrication process.

As shown in FIG. 1C, the third semiconductor substrate sample S3 which has a second oxide layer 2b (second layer). However, the third sample S3 is subject to the same contaminating process as that for the first sample S1. Therefore, contaminating metal 1c is present on the surface of the second layer 2b.

These samples S1 to S3 are dissolved all of the insulation layers 2 and 2b by HF vapor. The dissolved solutions are collected and analyzed by atomic absorption measurement device or ICP mass analyzing device for deriving metallic contamination amount. In this case, contamination amounts of respective samples becomes total contamination amount containing contamination in respective portions set out below.

At first, the contamination amount of the sample S3 is an amount of contaminating metal 1a deposited on the surface of the oxide layer 2b (this contamination amount is assumed as A). On the other hand, in the sample S1, assuming that a surface ratio of the exposed surface, namely surface coverage [1−(occupying ratio of the holes 2a)] is a, the contamination amount of metal present on the surface of the sample S1 becomes aA. Also, contamination amount of metal 1b present on the surface within the holes 2a of the sample S1 is assumed as B, and the contaminating metal 1c contained within the insulation layer 2 of the samples S1 and S2 is assumed as C. Then, the contamination amount of the sample S1 is aA (metal contamination amount on the surface of the oxide layer)+B (metal contamination amount on the surface within the hole)+C (metal contamination amount in the insulation layer). On the other hand, the contamination amount of the sample S2 is the metal contamination amount C contained in the insulation layer 2.

From respective values of the contamination amounts analyzed as set forth above, the contamination amount within the hole can be derived in the manner expressed by the following equation (3).

$$B \text{ (contamination amount within the hole)} = \text{contamination amount of the first semiconductor substrate sample } [aA+B+C] - \text{contamination amount of the second semiconductor substrate sample } [C] - \text{surface exposing ratio} \times \text{contamination amount of the third semiconductor substrate sample } [a \times A] \quad (3)$$

Thus, in the shown embodiment, irrespective of the opening diameter or depth of the hole, even in the fine hole and deep hole, the metal contamination amount residing within the hole can be measured with high sensitivity.

FIGS. 2A to 2G are sections showing fabrication process of the contaminated sample S1 and non-contaminated sample S2 having hole to be analyzed, in sequential order of steps.

Figure 2A:
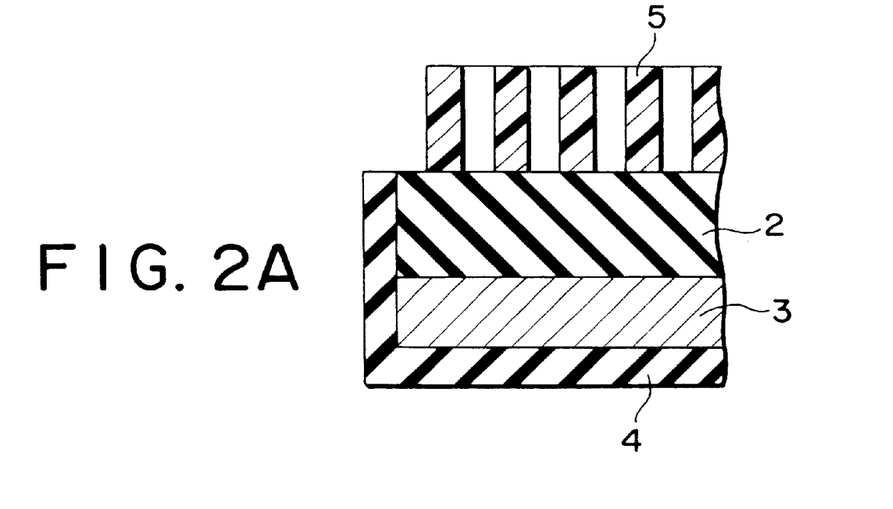
FIGS. 2A to 2G are sections showing fabrication process of first and second semiconductor substrate samples illustrated in sequential order.

As shown in FIG. 2A, on a Si wafer 3, an oxide layer 2 is deposited in a thickness of 1 $\mu$m for example, by CVD method. On the oxide layer 2, a resist 5 is deposited. Thereafter, predetermined hole pattern is formed in the resist 5.

On the other hand, on the side surfaces of the Si wafer 3 and the oxide layer 2 and on the back surface of the Si wafer 3, an oxide layer 4 is formed. A method for forming the oxide layer may be normal gas CVD method or HTO (High Temperature CVD Oxide) method. The oxide layer 4 may also be formed by thermal oxidation method.

Figure 2B:
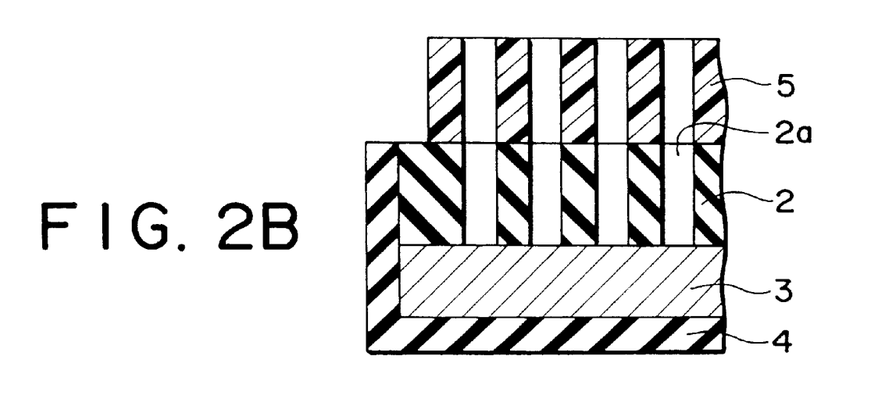

Next, as shown in FIG. 2B, with taking the resist pattern as a mask, with normal light exposure or EB exposure, holes 2a having opening diameter of 0.3 µm, for example, are formed in the oxide layer 2 on the Si wafer 3.

Number of the holes 2a to be formed is in the extent of 5 to $8\times10^8/cm^2$ in assumption of DRAM of 256 Mbit. With taking the resist 5 patterned by exposure as mask, dry etching of the oxide layer 2 is performed with employing a mixture gas of $CF_4$ and $CHF_3$.

Figure 2C:
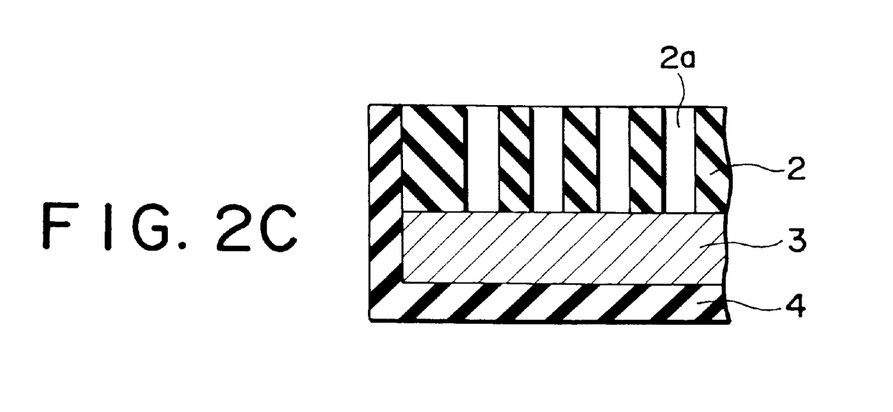

Next, as shown in FIG. 2C, the resist 5 is removed by oxygen plasma ashing from the sample formed with the holes 2a in the oxide layer 2 by dry etching. The residual slug of the resist is removed by washing with sulfonic hydrogen peroxide solution ($H_2SO_4:H_2O_2=5:1$, 130° C., 10 minutes, for example).

Figure 2D:
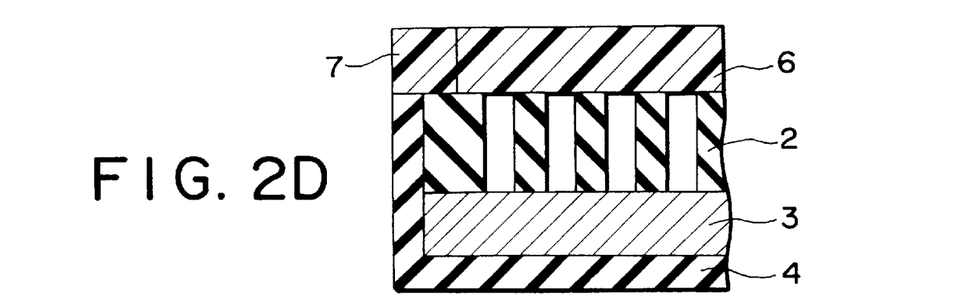

Then, as shown in FIG. 2D, in order to remove oxide layer 4 presenting on the back surface and side surface of the Si wafer 3, the surface of the Si wafer 3 is covered with a covering resist 6. Thereafter, with spinning the Si wafer 3, an organic solvent is dripped at the edge portion of the wafer 3, a portion 7 of the resist 6 in a range of about 3 mm from the edge of the wafer 3 is removed.

Figure 2E:
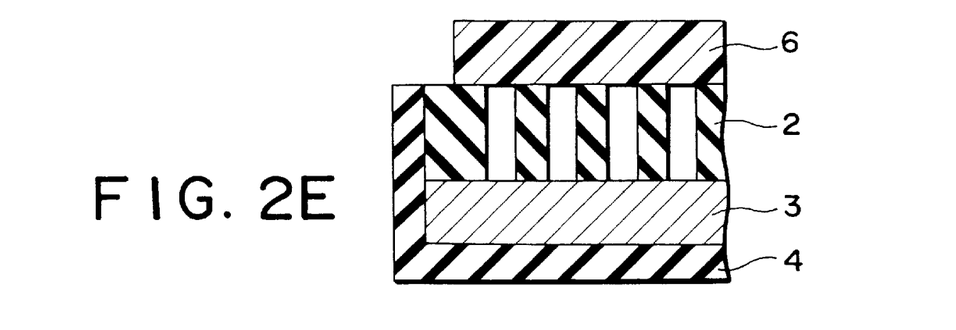

Then, as shown in FIG. 2E, after the portion 7 of the resist 6 is removed, the Si wafer 3 is dipped in a BHF solution for 5 to 10 minutes to remove the oxide layer 2 on the side surfaces of the Si wafer 3 and the oxide layer 4 on the back surface of the Si wafer 3.

Figure 2F:
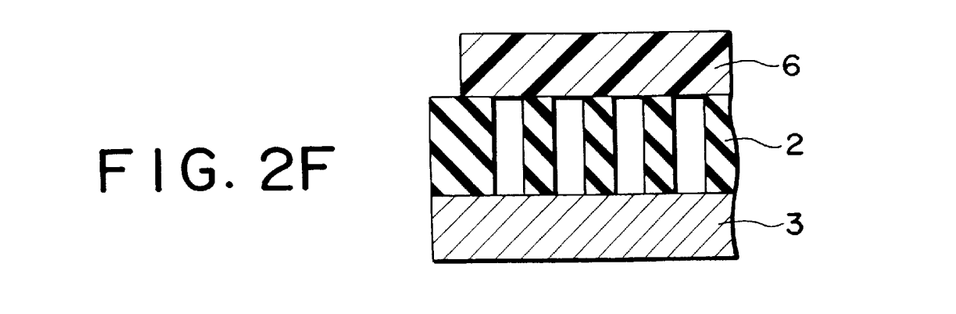
Figure 2G:
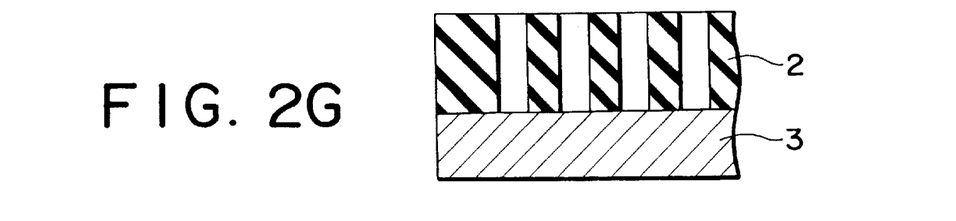

As shown in FIG. 2G, the covering resist 6 is removed by $O_2$ plasma ashing and the residual slug of the resist is removed by washing with sulfonic hydrogen peroxide solution ($H_2SO_4:H_2O_2=5:1$, 130° C., 10 minutes, for example).

Thus, the samples from which the oxide layers 4 on the side surface and back surface of Si wafer 3 and the resist 6 on the surface of Si wafer 3 are completely removed, are taken as the samples S1 and S2.

The reason why the oxide layer on the side surface and the back surface of the Si wafer 3 as set forth above is that, if the oxide layer 4 is present on the back surface and the side surface of the Si wafer 3, HF solution may penetrate into the back surface side during HF process for atomic absorption measurement to make it difficult to measure contaminant concentration only on the surface. Removing process of the oxide layer 4 on the back surface and the side surface of the Si wafer is essential when a method for forming the surface insulation layer is HTO method or thermal oxidation method, whereas is not so important in the case where the method for forming the surface insulation layer is CVD method wherein the oxide layer is not deposited on the back surface and the side surface.

Figure 3A:
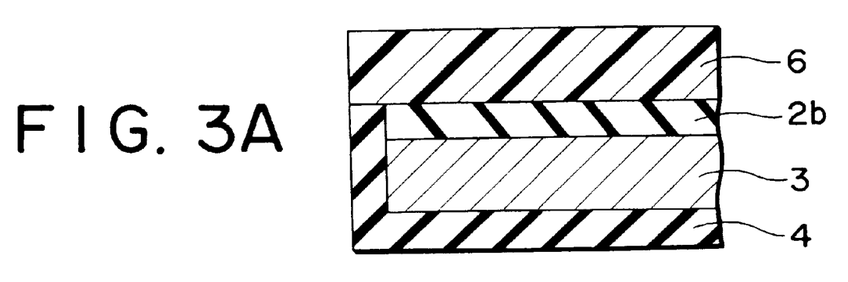
FIGS. 3A to 3D are sections showing fabrication process of a third semiconductor substrate sample illustrated in sequential order.

FIGS. 3A to 3D are sections showing a process of fabricating the third semiconductor substrate sample S3. At first, as shown in FIG. 3A, the oxide layer 2b is formed on the Si wafer 3. On the oxide layer 2b, a resist 6 is formed for covering. Then, similarly to FIG. 2D, in order to remove oxide layer 4 on the back surface and the side surface of the Si wafer 3, the surface of the Si wafer 3 is covered with the covering resist 6.

Figure 3B:
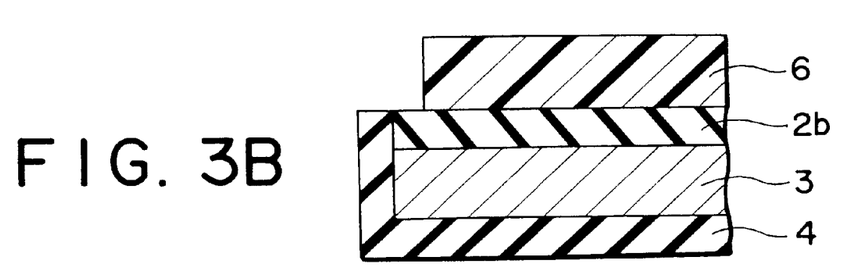

Then, as shown in FIG. 3B, with spinning the Si wafer 3, the organic solvent is dripped on the edge portion of the wafer 3 to remove the resist portion at the peripheral portion of the Si wafer 3.

Figure 3C:
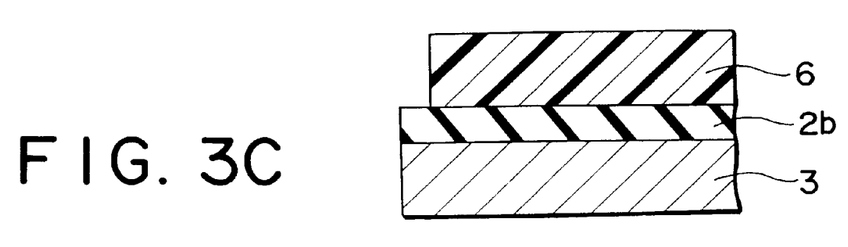

Next, as shown in FIG. 3C, similarly to the process of FIG. 2F, the Si wafer 3 removed the edge portion of the resist is dipped in the BHF solution for 5 to 10 minutes for removing the oxide layer 4 on the side surface and the back surface.

Figure 3D:
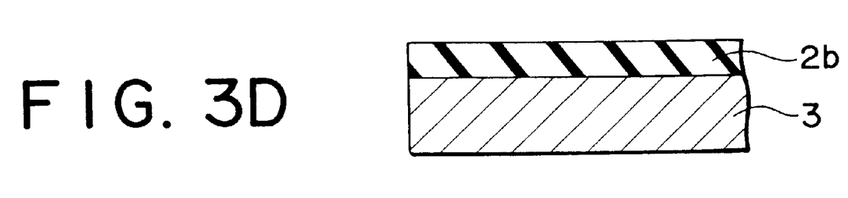

Subsequently, as shown in FIG. 3D, similarly to the process of FIG. 2G, the covering resist 6 is removed by $O_2$ plasma ashing and the residual slug of the resist is removed by washing with sulfonic hydrogen peroxide solution ($H_2SO_4:H_2O_2=5:1$, 130° C., 10 minutes, for example).

By this, the sample S3 completely removed the oxide layer 4 on the side surface and the back surface of the Si wafer 3 can be obtained. In this case, the oxide layer 2b is preferably in a thickness of less than or equal to 50 nm in order to restrict affect of metal contamination amount present in the oxide layer 2b. The sample thus prepared becomes the sample S3 before contamination.

Figure 4:
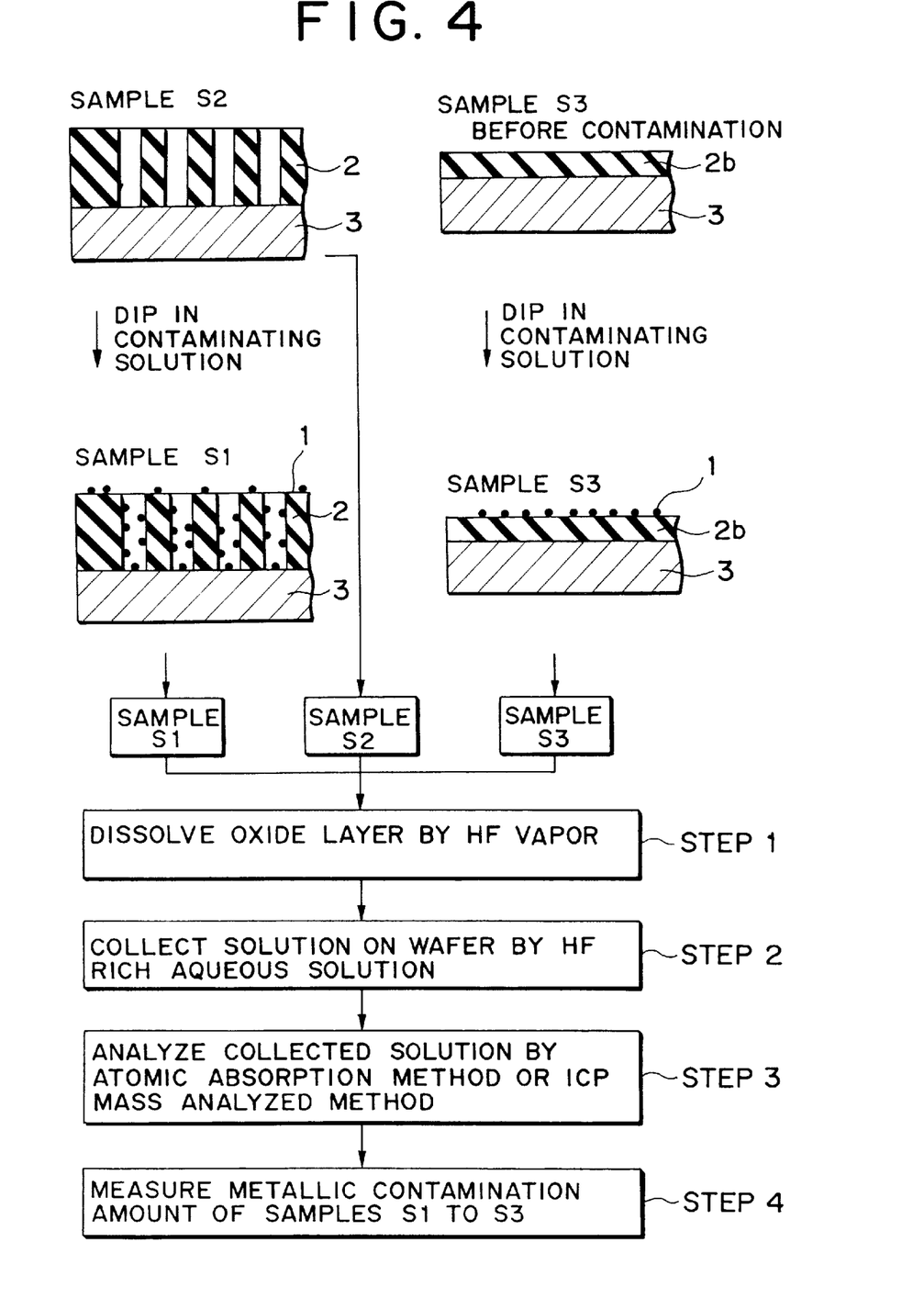
FIG. 4 is an illustration showing an analyzing method of the semiconductor substrate samples after contamination.

Next, with reference to FIG. 4, result of test performed for verification of the effect of the method of the present invention will be described. FIG. 4 is a flowchart of the test. As shown in FIG. 4, the semiconductor substrate sample shown in FIG. 2G and the semiconductor substrate sample shown in FIG. 3D were dipped in ammonia hydrogen peroxide solution ($NH_4OH:H_2O_2:H_2O=1:4:20$, 65° C., 10 minutes) containing Fe (100 ppb) for forced contamination by Fe. By this, the contaminated S1 and the contaminated S3 were obtained.

The contaminated samples S1 and S3 and non-contaminated sample S2 were analyzed the contamination amount by atomic absorption measurement. At first, to respective samples S1 to S3, rich HF vapor is blown to remove all of the surface oxide layers 2 and 2b (step 1). Then, solution on the Si wafer 3 was collected with HF rich aqueous solution (step 2), analysis of Fe concentration was performed by atomic absorption method (step 3).

As a result of measurement, analyzed value $8\times10^{13}$ (atoms/cm²) was obtained from the sample S1, analyzed value $5\times10^9$ (atoms/cm²) was obtained from the sample S2, and analyzed value $2\times10^{13}$ (atoms/cm²) was obtained from the sample S3. Since the occupied area of the holes was 0.25, a=0.75. From the obtained value, as expressed in the following equation (3), the metal contamination amount is calculated (step 4).

B (contamination amount within the hole) =contamination amount of the first semiconductor substrate sample [aA+B+C]−contamination amount of the second semiconductor substrate sample [C]−surface exposing ratio ×contamination amount of the third semiconductor substrate sample [a×A]= $8\times10^{13}-5\times10^9-0.75\times2\times10^{13}=6.5\times10^{13}$+tm (3)

As set forth above, the contamination amount within the hole could be obtained as $6.5\times10^{13}$ (atoms/cm²).

Next, example of test for contamination removal effect in the hole by acid washing will be described. The removal effect test was performed by washing the samples S1 and S3 with hydrochloric hydrogen peroxide solution. The result is shown hereinafter. A value $2\times10^{10}$ (atoms/cm²) was obtained from the sample S1, a value $5\times10^9$ (atoms/cm²) was obtained from the sample S2, and analyzed value $3\times10^9$ (atoms/cm²) was obtained from the sample S3. The ratio a is assumed to be 0.75. Then, B (contamination amount within the hole) is obtained as follow.

$$B \text{ (contamination amount within the hole)} = 2\times10^{10} - 5\times10^9 - 0.75\times3\times10^9 = 1.125\times10^{10}$$

As set forth above, the residual Fe contamination amount after acid washing can be known.

Figure 5:
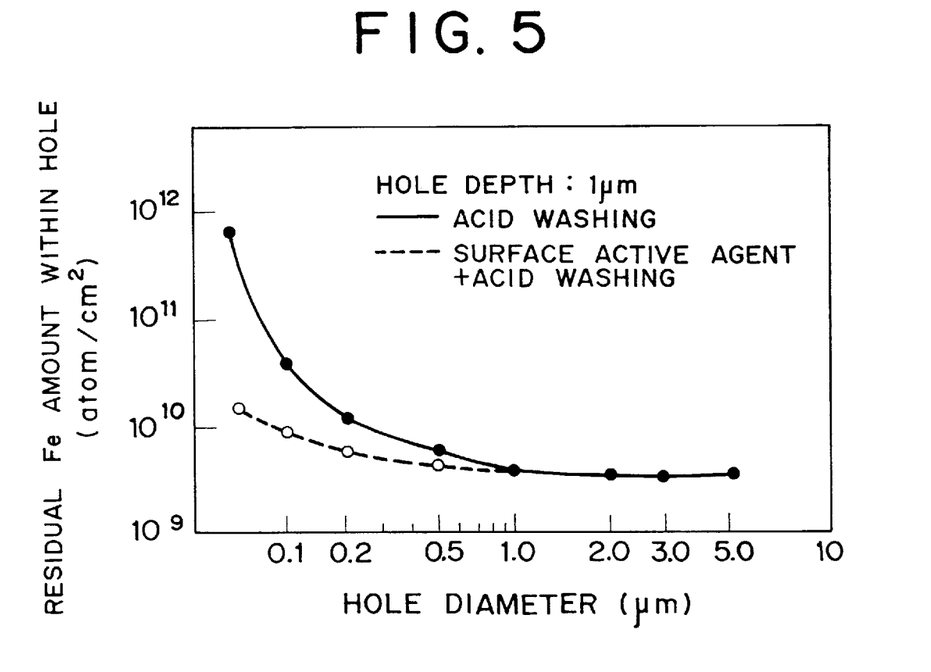
FIG. 5 is a characteristic chart showing residual metallic contaminant amount within a hole with respect to an opening diameter of the hole.

FIG. 5 is an illustration showing a hole diameter dependency of residual Fe amount within the hole after washing in the contact hole in the depth of 1 µm employing the foregoing measuring method. From FIG. 5, it is appreciated that residual Fe amount within the hole is increased according to down-sizing of the hole diameter.

On the other hand, the broken line of FIG. 5 shows a result of checking of the hole diameter dependency similarly with respect to the case where the surface active agent is added to the acid washing solution. From the result shown in FIG. 5, influence of down-sizing of the hole can be reduced by adding the surface active agent.

Figure 6:
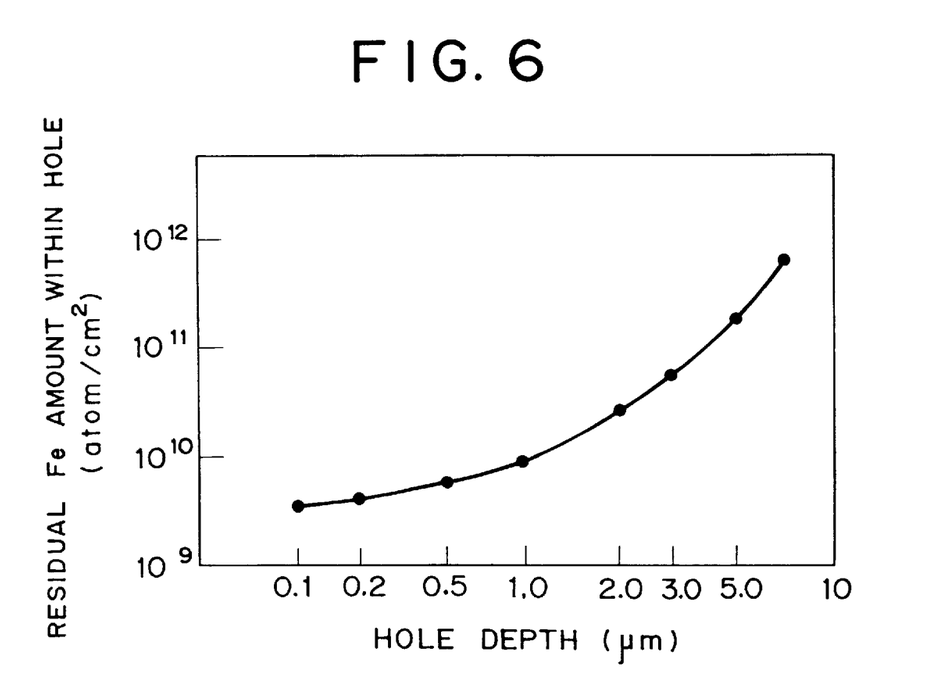
FIG. 6 is a characteristic chart showing residual metallic contaminant amount within a hole with respect to a depth of the hole.

On the other hand, FIG. 6 is an illustration showing a hole depth dependency of residual Fe amount within the hole after washing in the hole having diameter of 0.3 μm. From FIG. 6, it should be appreciated that the residual Fe amount is increased according to increasing of depth of the hole. It should be appreciated that while the foregoing description has been given in terms of the embodiment employing Fe as contaminating metal, similar measurement can be done with respect to the metal of Cu, Ni, Cr, Al, Na, Ca or the like.

Although the invention has been illustrated and described with respect to exemplary embodiment thereof, it should be understood by those skilled in the art that the foregoing and various other changes, omissions and additions may be made therein and thereto, without departing from the spirit and scope of the present invention. Therefore, the present invention should not be understood as limited to the specific embodiment set out above but to include all possible embodiments which can be embodied within a scope encompassed and equivalents thereof with respect to the feature set out in the appended claims.

What is claimed is:

1. A contamination analyzing method within a hole in the semiconductor device comprising the steps of:

preparing first and second semiconductor substrate samples having a first layer with holes on said first and second semiconductor substrate samples and a third semiconductor substrate sample having a second layer with no hole on said third semiconductor substrate;

subjecting said first semiconductor substrate sample and said third semiconductor substrate sample to the same contaminating process for contaminating the surface of said first layer of said first semiconductor substrate sample and the surface within said hole, and the surface of said second layer of said third semiconductor substrate sample;

dissolving all of said first and second layers of said first to third semiconductor substrate samples, collecting solutions after dissolving, analyzing amount of contaminating material contained in respective solutions for obtaining first to third contamination amount with respect to said first to third semiconductor substrate samples; and deriving a contamination amount within the hole of said first semiconductor substrate sample from said first to third contamination amounts.

2. A contamination analyzing method as set forth in claim 1, wherein the contamination amount in the hole is derived on the basis of said first, second and third contamination amount from an equation:

$$\text{contamination amount in hole} = \text{first contamination amount} - \text{second contamination amount} - (\text{surface exposing ratio}) \times (\text{third contamination amount})$$

wherein the surface exposing ratio is a surface ratio [1−(occupying ratio of the hole)] of exposed surface in the first semiconductor substrate sample.

3. A contamination analyzing method as set forth in claim 1, wherein when the contamination amount of said second semiconductor substrate sample is much smaller in comparison with the contamination amount of said first and third semiconductor substrate samples, the contamination amount within the hole is derived from an equation:

$$\text{contamination amount in hole} = \text{first contamination amount} - (\text{surface exposing ratio}) \times (\text{third contamination amount}).$$

4. A contamination analyzing method as set forth in claim 1, wherein, before dissolving the layer formed on said first, second and third semiconductor substrate sample, layers depositing on the side surface and back surface of each semiconductor substrate sample are removed.

5. A contamination analyzing method as set forth in claim 1, wherein all of said first and second layers are dissolved by a vapor containing HF.

6. A contamination analyzing method as set forth in claim 1, wherein said contaminating material is a metal.

7. A contamination analyzing method as set forth in claim 1, wherein the contaminant amount contained in the dissolved solution is measured by one of atomic absorption measurement device and an ICP analyzing device.

8. A contamination analyzing method as set forth in claim 1, wherein said first to third semiconductor substrate samples are formed of Si and said first and second layers are silicon oxide layers of Si.

9. A contamination analyzing method as set forth in claim 1, wherein said contaminating process has a step of dipping said first and third semiconductor substrate samples within contaminating solution.

* * * * *